(12) United States Patent
Kopelman

(10) Patent No.: US 11,752,030 B2
(45) Date of Patent: *Sep. 12, 2023

(54) SYSTEMS AND METHODS FOR POSITIONING A PATIENT'S MANDIBLE IN RESPONSE TO SLEEP APNEA STATUS

(71) Applicant: Align Technology, Inc., San Jose, CA (US)

(72) Inventor: Avi Kopelman, Palo Alto, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/539,113

(22) Filed: Nov. 30, 2021

(65) Prior Publication Data

US 2022/0257408 A1 Aug. 18, 2022

Related U.S. Application Data

(60) Continuation of application No. 16/420,017, filed on May 22, 2019, now Pat. No. 11,207,208, which is a
(Continued)

(51) Int. Cl.
*A61F 5/56* (2006.01)

(52) U.S. Cl.
CPC .................................... *A61F 5/566* (2013.01)

(58) Field of Classification Search
CPC ...... A61F 5/56; A61F 2005/563; A61F 5/566; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61F 5/58; Y10S 602/902; A61N 2/00; A61N 2/002; A61N 2/004; A61N 2/006;
(Continued)

(56) References Cited

U.S. PATENT DOCUMENTS 5,820,368 A 10/1998 Wolk
6,386,864 B1 5/2002 Kuo
(Continued)

*Primary Examiner* — Tarla R Patel
(74) *Attorney, Agent, or Firm* — FISHERBROYLES, LLP

(57) ABSTRACT

Systems, methods, devices, and apparatus for positioning a patient's mandible in response to sleep apnea status are provided herein. In one aspect, a system for monitoring and treating sleep apnea in a patient comprises one or more sensors configured to monitor the patient for symptoms associated with sleep apnea; an intraoral appliance worn by the patient, one or more processors, and memory comprising instructions executable by the one or more processors to cause the one or more processors to: receive a set of sensor data from the one or more sensors, detect, using a machine learning algorithm, onset of a sleep apnea event based on the set of sensor data, and transmit a control signal to the intraoral appliance to cause the intraoral appliance to displace a lower jaw of the patient from a first position to a second position in order to treat the sleep apnea event.

20 Claims, 8 Drawing Sheets

Related U.S. Application Data division of application No. 14/992,175, filed on Jan. 11, 2016, now Pat. No. 10,537,463.

(60) Provisional application No. 62/161,798, filed on May 14, 2015, provisional application No. 62/103,010, filed on Jan. 13, 2015.

(58) Field of Classification Search
CPC ........ A61N 2/008; A61N 1/40; G09B 19/003; G09B 23/28; Y10T 29/49826; A61C 7/08; A61C 19/063; A61B 5/4547; A61B 5/4552; A61B 5/4557; A61B 5/682; A61B 5/0534; A63B 71/085; A63B 2071/086; A63B 2017/088
See application file for complete search history.

(56) References Cited

U.S. PATENT DOCUMENTS

| | | |
|---|---|---|
| 6,454,565 B2 | 9/2002 | Phan et al. |
| 6,471,511 B1 | 10/2002 | Chishti et al. |
| 6,607,382 B1 | 8/2003 | Kuo et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,537,463 B2* | 1/2020 | Kopelman ............ A61F 5/566 |
| 10,548,700 B2 | 2/2020 | Fernie |
| 10,555,792 B2 | 2/2020 | Kopelman et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 11,103,330 B2 | 8/2021 | Webber et al. |
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 11,259,896 B2 | 3/2022 | Matov et al. |
| 11,273,011 B2 | 3/2022 | Shanjani et al. |
| 11,278,375 B2 | 3/2022 | Yuxiang et al. |
| 11,318,667 B2 | 5/2022 | Mojdeh et al. |
| 11,331,166 B2 | 5/2022 | Morton et al. |
| 11,344,385 B2 | 5/2022 | Morton et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0067334 A1 | 3/2014 | Kuo |
| 2014/0114146 A1* | 4/2014 | Hanewinkel ............ A61B 5/394 |
| | | 600/301 |
| 2014/0323839 A1* | 10/2014 | McCreery ............ A61B 5/4552 |
| | | 600/407 |
| 2015/0265376 A1 | 9/2015 | Kopelman |
| 2015/0366638 A1 | 12/2015 | Kopelman et al. |
| 2016/0193014 A1 | 7/2016 | Morton et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007366 A1 | 1/2017 | Kopelman et al. |
| 2017/0007386 A1 | 1/2017 | Mason et al. |
| 2017/0135792 A1 | 5/2017 | Webber |

(56) References Cited

U.S. PATENT DOCUMENTS

| | | |
|---|---|---|
| 2017/0135793 A1 | 5/2017 | Webber et al. |
| 2017/0165032 A1 | 6/2017 | Webber et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0046297 A1 | 2/2019 | Kopelman et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0343606 A1 | 11/2019 | Wu et al. |
| 2020/0000553 A1 | 1/2020 | Makarenkova et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |
| 2021/0147672 A1 | 5/2021 | Cole et al. |

\* cited by examiner

SYSTEMS AND METHODS FOR POSITIONING A PATIENT'S MANDIBLE IN RESPONSE TO SLEEP APNEA STATUS

CROSS-REFERENCE

This application is a continuation of U.S. application Ser. No. 16/420,017, filed May 22, 2019, now U.S. Pat. No. 11,207,208, issued Dec. 28, 2021, which is a divisional application of U.S. application Ser. No. 14/992,175, filed Jan. 11, 2016, now U.S. Pat. No. 10,537,463 issued Jan. 21, 2020, which claims the benefit of U.S. Provisional Application No. 62/161,798, filed May 14, 2015, and U.S. Provisional Application No. 62/103,010, filed Jan. 13, 2015, the disclosures of each are incorporated herein by reference in their entirety.

BACKGROUND

Obstructive sleep apnea (hereinafter "OSA") is a medical condition characterized by complete or partial blockage of the upper airway during sleep. The obstruction may be related to relaxation of soft tissues and muscles in or around the throat (e.g., the soft palate, back of the tongue, tonsils, uvula, and pharynx) during sleep. OSA episodes may occur multiple times per night and disrupt the patient's sleep cycle. Suffers of chronic OSA may experience sleep deprivation, excessive daytime sleepiness, chronic fatigue, headaches, snoring, and hypoxia.

Mandibular advancement devices (also referred to as mandibular splints or mandibular advancement splints) have been proposed to treat OSA. A mandibular advancement device is worn in the mouth over the teeth of the upper and/or lower jaws. The device treats sleep apnea by advancing the lower jaw in an anterior direction relative to the upper jaw. This advancement may tighten the tissues of the upper airway, and inhibit airway obstruction during sleep.

In some instances, however, existing mandibular advancement devices for treating OSA may produce undesirable side effects, such as tooth repositioning, jaw discomfort, and muscle strain. For these reasons, it would be desirable to provide improved methods and apparatus for treating obstructive sleep apnea and snoring. In particular, it would be desirable to provide improved methods and apparatus which provide mandibular advancement with decreased undesirable side effects, such as tooth repositioning, jaw discomfort, and muscle strain.

SUMMARY

Systems, methods, devices, and apparatus described herein provide improved treatment of obstructive sleep apnea with decreased undesirable side effects, such as tooth repositioning, jaw discomfort, and muscle strain. A mandibular advancement device can be combined with patient monitoring and customized treatment to treat obstructive sleep apnea and snoring with improved detection of symptoms associated with sleep apnea and improved treatment of sleep apnea based on or in response to a patient's sleep apnea status. The improved detection and treatments provided herein can be patient-customized with machine learning algorithms that accurately detect the onset and termination of sleep apnea events, and that improve the position and duration of jaw displacement to treat sleep apnea effectively while decreasing unwanted side effects, such as jaw soreness, temporomandibular joint (TMJ) soreness, tooth pain, patient discomfort and/or unwanted repositioning of teeth.

Systems as described herein comprise sensors that monitor a patient for symptoms associated with sleep apnea, and processors that execute instructions to receive data from the sensors and detect sleep apnea events more accurately in response to the received patient data. Instructions executed by the processors can comprise machine learning algorithms that optimize both the detection of symptoms and the course of treatment based on or in response to patient-specific factors and data, such as previous sleep apnea events of the patient. Processors as described herein can execute instructions to transmit control signals to an intraoral appliance in response to detection of sleep apnea symptoms. The control signals can cause the intraoral appliance to displace the lower jaw to a position and for a duration provided by the machine learning algorithm to treat the sleep apnea event effectively while decreasing unwanted side effects.

In one aspect, a system for monitoring and treating sleep apnea in a patient is provided, the system comprising: one or more sensors configured to monitor the patient for symptoms associated with sleep apnea; an intraoral appliance wearable by the patient; one or more processors; and memory comprising instructions executable by the one or more processors to cause the one or more processors to: receive a set of sensor data from the one or more sensors, detect, using a machine learning algorithm, onset of a sleep apnea event based on the set of sensor data, and transmit a control signal to the intraoral appliance to cause the intraoral appliance to displace a lower jaw of the patient from a first position to a second position in order to treat the sleep apnea event.

In another aspect, a system for monitoring and treating sleep apnea in a patient is provided, the system comprising: one or more processors; and memory comprising instructions executable by the one or more processors to cause the one or more processors to: receive a set of sensor data from one or more sensors, detect onset of a sleep apnea event in response to the set of sensor data, and transmit a control signal to an intraoral appliance to displace a lower jaw of the patient from a first position to a second position in order to treat the sleep apnea event.

In another aspect, a method for monitoring and treating sleep apnea in a patient is provided, the method comprising: receiving a set of sensor data from one or more sensors configured to monitor the patient for symptoms associated with sleep apnea; detecting an onset of a sleep apnea event in response to the set of sensor data; and transmitting a control signal to an intraoral appliance worn by the patient to displace a lower jaw of the patient from a first position to a second position in order to treat the sleep apnea event.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
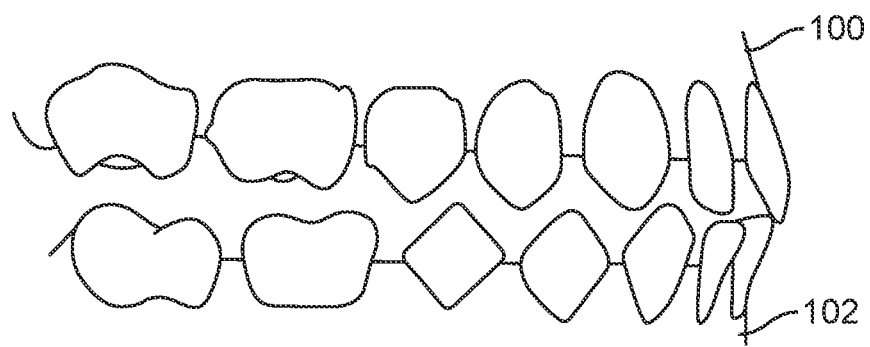
FIG. 1A illustrates a patient's upper and lower jaws in a habitual occlusal position, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

As used herein the term "and/or" is used as a functional word to indicate that two words or expressions are to be taken together or individually. For example, A and/or B encompasses A alone, B alone, and A and B together.

Systems, methods, devices and apparatus for positioning a patient's mandible in response to sleep apnea status are provided herein. In various aspects, systems are provided for monitoring and treating sleep apnea in a patient, the systems comprising: one or more sensors configured to monitor the patient for symptoms associated with sleep apnea; an intraoral appliance worn by the patient; one or more processors; and memory comprising instructions executable by the one or more processors to cause the one or more processors to: receive a set of sensor data from the one or more sensors, detect, using a machine learning algorithm, onset of a sleep apnea event based on the set of sensor data, and transmit a control signal to the intraoral appliance to cause the intraoral appliance to displace a lower jaw of the patient from a first position to a second position in order to treat the sleep apnea event.

In various aspects, methods are provided for monitoring and treating sleep apnea in a patient, the methods comprising: receiving a set of sensor data from one or more sensors configured to monitor the patient for symptoms associated with sleep apnea; detecting, using a machine learning algorithm executed by one or more processors, onset of a sleep apnea event based on the set of sensor data; and transmitting a control signal to an intraoral appliance worn by the patient to cause the intraoral appliance to displace a lower jaw of the patient from a first position to a second position in order to treat the sleep apnea event.

In various aspects, one or more non-transitory computer-readable storage media are provided, having stored thereon instructions that, when executed by one or more processors of a system for monitoring and treating sleep apnea in a patient, cause the system to at least: receive a set of sensor data from one or more sensors configured to monitor the patient for symptoms associated with sleep apnea; detect, using a machine learning algorithm, onset of a sleep apnea event based on the set of sensor data; and transmit a control signal to an intraoral appliance worn by the patient to cause the intraoral appliance to displace a lower jaw of the patient from a first position to a second position in order to treat the sleep apnea event.

The one or more sensors can be configured to measure one or more of breathing sounds, snoring sounds, breathing rate, respiratory air flow, chest expansion, oxygen level, cardiac data, or sleeping position, or combinations thereof. The set of sensor data can be indicative of symptoms associated with the onset of the sleep apnea event. The machine learning algorithm can be customized to the patient. The machine learning algorithm can be customized to the patient using data of previous sleep apnea events of the patient. The machine learning algorithm can be customized to the patient using data of previous sleep patterns of the patient. The instructions can further cause the system to identify a discrepancy between a current sleeping pattern of the patient and the previous sleep patterns of the patient and generate an alert indicative of the discrepancy.

The methods can further comprise: identifying, with aid of the one or more processors, a discrepancy between a current sleeping pattern of the patient and the previous sleep patterns of the patient; and generating, with aid of the one or more processors, an alert indicative of the discrepancy. The first position can be a habitual jaw position and the second position can be an advanced jaw position.

The instructions can further cause the system to: receive a second set of sensor data from the one or more sensors; detect, using the machine learning algorithm, termination of the sleep apnea event based on the second set of sensor data; and transmit a second control signal to the intraoral appliance to cause the intraoral appliance to displace the lower jaw of the patient from the second position to the first position. The instructions can further cause the system to determine the second position for the lower jaw using the machine learning algorithm. The instructions can further cause the system to: receive a third set of sensor data from the one or more sensors while the lower jaw is in the second position; and determine effectiveness of the second position of the lower jaw in treating the sleep apnea event based on the third set of sensor data. The instructions can further cause the system to update the machine learning algorithm based on the determined effectiveness. The instructions can further cause the system to: determine, using the machine learning algorithm, a modified position of the lower jaw to improve the effectiveness of treating the sleep apnea event; and transmit a third control signal to the intraoral appliance to displace the lower jaw to the modified position.

The methods can further comprise: receiving, with aid of the one or more processors, a second set of sensor data from the one or more sensors; detecting, with aid of the one or more processors and using the machine learning algorithm, termination of the sleep apnea event based on the second set of sensor data; and transmitting, with aid of the one or more processors, a second control signal to the intraoral appliance to cause the intraoral appliance to displace the lower jaw of the patient from the second position to the first position. The methods can further comprise determining the second position for the lower jaw using the machine learning algorithm. The methods can further comprise receiving, with aid of the one or more processors, a third set of sensor data from the one or more sensors while the lower jaw is in the second position; and determining, with aid of the one or more processors, effectiveness of the second position of the lower jaw in treating the sleep apnea event based on the third set of sensor data. The methods can further comprise updating the machine learning algorithm based on the determined effectiveness. The methods can further comprise determining, with aid of the one or more processors and using the machine learning algorithm, a modified position of the lower jaw to improve the effectiveness of treating the sleep apnea event; and transmitting, with aid of the one or more processors, a third control signal to the intraoral appliance to displace the lower jaw to the modified position.

The second set of sensor data can be indicative of lessening of symptoms associated with the sleep apnea event. The intraoral appliance can comprise an upper shell shaped to fit on an upper jaw of the patient; a lower shell shaped to fit on the lower jaw of the patient; and an advancement apparatus coupling the upper shell and the lower shell, wherein the advancement apparatus is configured to displace the lower shell relative to the upper shell in response to control signals from the one or more processors in order to displace the lower jaw. The advancement apparatus can be configured to displace the lower shell to a plurality of different positions relative to the upper shell. The advancement apparatus can comprise: an upper advancement structure coupled to the upper shell; a lower advancement structure coupled to the lower shell; and an actuator configured to bring the lower advancement structure and upper advancement structure into engagement with each other in response to the control signals, thereby displacing the lower shell relative to the upper shell. The advancement apparatus can comprise: a tether element coupling the upper shell and the lower shell; and an actuator configured to adjust a length of the tether element extending between the upper shell and the lower shell in response to the control signals, thereby displacing the lower shell relative to the upper shell.

In various aspects, intraoral appliances are provided for treating sleep apnea in a patient via mandibular advancement, the apparatus comprising: an upper shell shaped to fit on an upper jaw of the patient; a lower shell shaped to fit on a lower jaw of the patient; and an advancement apparatus coupling the upper shell and the lower shell, wherein the advancement apparatus is configured to displace the lower shell relative to the upper shell in response to control signals received from one or more processors in order to displace the lower jaw.

In various aspects, the present disclosure provides a patient-specific approach to sleep apnea using a feedback control system adapted to monitor the sleep apnea status of the patient and actively control the mandibular position to respond to sleep apnea incidents and reduce snoring.

In various aspects, a system for mandibular advancement comprises an oral appliance, a sensor, and a controller and/or processor. The oral appliance can be configured to selectively advance a patient's mandible relative to the upper jaw (maxilla).

In various aspects, the present disclosure provides a "motorized" intraoral appliance configured to selectively advance and retract a patient's mandible relative to the patient's upper jaw (maxilla). When the patient is free from snoring and other symptoms of sleep apnea, the oral appliances can leave the mandible in its retracted or "free" configuration. The present disclosure, however, provides for monitoring the sleep apnea status of the patient and, when the onset of an apnea event is detected or predicted, the intraoral appliance can be activated to advance the mandible to effect treatment. Conversely, when cessation of the apnea event is detected or after a predetermined period of time, the system may optionally allow the mandible to retract.

In various aspects, an oral appliance comprises an upper anchor, a lower anchor, and a motor or other mechanism configured to selectively advance and retract the lower attachment relative to the upper attachment. The oral appliance can be particularly intended to operate together with the system just described where the motor or other mechanism may be controlled in response to a signal generated, typically by a sensor and controller and/or processor, in response to symptoms associated with sleep apnea.

In various aspects, a method for advancing a patient's mandible to treat sleep apnea comprises monitoring the patient for symptoms of sleep apnea, generating a signal when the patient's sleep apnea status changes, and selectively advancing and/or retracting a lower anchor secured to the patient's mandible relative to an upper anchor secured to the patient's upper jaw.

In various aspects, systems, methods, devices and apparatus described herein comprise systems for mandibular advancement, said systems comprising: an oral appliance configured to advance a patient's mandible relative to the upper jaw; a sensor configured to detect when the patient can benefit from mandible advancement; and a controller and/or processor which receives a signal from the sensor when the patient can benefit from mandibular advancement and which delivers a signal to the oral appliance to advance or retract the mandible. The oral appliance can comprise: an upper anchor configured to be secured to the patient's upper jaw; a lower anchor configured to be secured to the patient's lower jaw; and a motor coupled between the upper and lower anchors and configured to respond to the signal delivered by the controller and/or processor to advance or retract the mandible. The sensor can be configured to sense at least one of breathing sounds, respiratory air flow, cardiac data, and sleep position. The systems can further comprise an external device which includes the sensor. The sensor can be incorporated in the controller and/or processor. The sensor can be incorporated in the oral appliance. The controller and/or processor can be configured to deliver a signal to the oral appliance to advance the mandible when the controller and/or processor receives a signal from the sensor associated with an onset of an apnea event. The controller and/or processor can be further configured to deliver a signal to the oral appliance to retract the mandible when the controller and/or processor receives a signal from the sensor associated with a lessening of the apnea event. The controller and/or processor can be further configured to deliver a signal to the oral appliance to retract the mandible after a preselected time has passed. The controller and/or processor can be configured to collect data on the patient's apnea patterns over time and use such data to predict an onset of an apnea event.

In various aspects, systems, methods, devices and apparatus described herein comprise oral appliances comprising: an upper anchor which couples to the patient's upper jaw; a lower anchor which couples to the patient's mandible; and a motor configured to selectively advance and retract the lower anchor relative to the upper anchor in response to a signal generated in response to symptoms associated with sleep apnea. The upper and lower anchors can be configured to be removably secured over the patient's teeth. The upper and lower anchors can be configured to be affixed to the patient's upper jaw bone and mandible, respectively. The motor can comprise a rotor on one of the upper and lower anchors and a follower on the other of the anchors. The motor can comprise a translator on one of the upper and lower anchors and a follower on the other of the anchors. The motor can comprise a spindle on one of the upper and lower anchors and a tether which has one end mounted to be reeled in and out by the spindle and another end attached to the other of the anchors.

In various aspects, systems, methods, devices and apparatus described herein comprise methods for advancing a patient's mandible to treat sleep apnea, said methods comprising: monitoring the patient for symptoms of sleep apnea status; generating a signal when the patient's sleep apnea status changes; and selectively advancing a lower anchor secured to the patient's mandible relative to an upper anchor secured to the patient's upper jaw. Monitoring can comprise tracking at least one of breathing sounds, respiratory air flow, cardiac data, and sleep position. Monitoring can be performed by a sensor external to the patient. Monitoring can be performed by a sensor on an appliance worn by the patient. Generating can comprise producing a signal to advance the mandible in response to detecting symptoms associated with an onset of an apnea event. Generating can comprise producing a signal to retract the mandible in response to detecting a lessening of symptoms associated with an apnea event. Generating can comprise producing a signal to retract the mandible after a preselected time has passed. The method can further comprise collecting data on the patient's apnea patterns over time and using such collected data to predict an onset of an apnea event. Selectively advancing the anchor can comprise activating a motor coupled between the lower and upper anchors.

Mandibular Advancement Appliances

Turning now to the drawings, in which like numbers designate like elements in the various figures, FIG. 1A illustrates an upper jaw 100 and a lower jaw 102 of a patient in a habitual occlusal position, in accordance with embodiments. The habitual occlusal position can correspond to the normally closed position of the upper and lower jaws 100, 102. Patients suffering from sleep apnea may experience restricted airflow due to blockage of the upper airway if the upper and lower jaws 100, 102 remain in their habitual occlusal relationship during sleep due to relaxation of soft tissues in or around the upper airway.

Figure 1B:
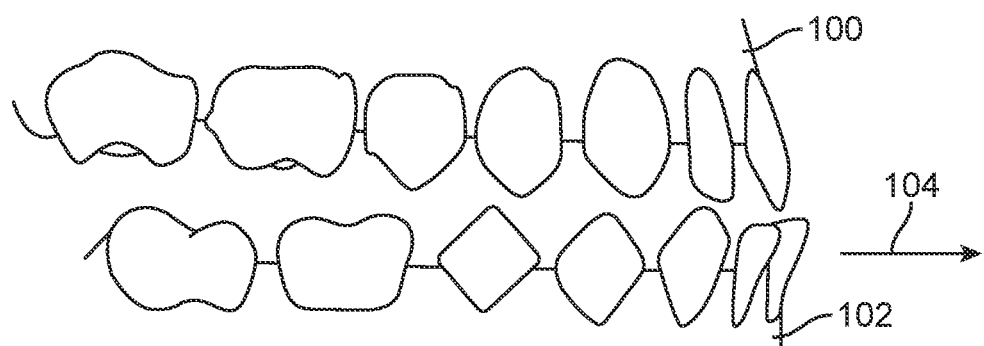
FIG. 1B illustrates a patient's upper and lower jaws in a "mandible-advanced" occlusal position, in accordance with embodiments.

FIG. 1B illustrates the upper jaw 100 and lower jaw 102 in a "mandible-advanced" occlusal position, in accordance with embodiments. In the advanced position, the lower jaw 102 has been displaced from its habitual position along an anterior direction (indicated by arrow 104) such that the lower jaw 102 is now positioned anteriorly relative to the upper jaw 100. The advanced position of the lower jaw 102 can be used to tighten the soft tissues of the upper airway, thus maintaining unobstructed airflow during sleep.

In some embodiments, an intraoral appliance (also referred to herein as a mandibular advancement appliance, mandibular advancement device, or mandibular advancement apparatus) is wearable by the patient in the order to displace the lower jaw anteriorly relative to the upper jaw to treat sleep apnea. The intraoral appliance can be a patient-removable appliance (e.g., the patient can place and remove the appliance without aid from a practitioner) that is insertable into the patient's mouth prior to sleep so as to maintain the lower jaw in an advanced position during sleep, and is removable from the patient's mouth while the patient is awake to allow for normal activity. In alternative embodiments, the intraoral appliance can include one or more components that are not patient-removable (e.g., attachments or brackets affixed to one or more teeth, anchoring devices positioned in the tissue of the intraoral cavity such as bone).

The intraoral appliance can take a wide variety of forms. In some embodiments, the intraoral appliance includes at least one appliance shell having a plurality of cavities shaped to receive teeth of a single jaw of the patient (e.g., the upper jaw or the lower jaw). The appliance can be fabricated with one or more of many materials such as metal, glass, reinforced fibers, carbon fiber, composites, reinforced composites, aluminum, biological materials, or combinations thereof. The appliance can be manufactured in many ways, such as with thermoforming or direct fabrication. Alternatively or in combination, the appliance can be fabricated with machining, such as an appliance fabricated from a block of material with computer numeric control (CNC) machining. Alternatively or in combination, additive manufacturing processes such as stereolithography or 3-D printing can be used to fabricate the appliances described herein.

The intraoral appliance may comprise any design which is compatible with providing anchoring or attachment to the patient's upper jaw and mandible (lower jaw). For example, the shells or anchors of an appliance may resemble conventional retainers which are formed to conform to the patient's teeth. Similarly, the shells may comprise "aligners" of the type intended for orthodontic repositioning. Exemplary tooth repositioning appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Such retainers and aligners may be formed from conventional materials, such as acrylates, thermoform materials, composite materials, and may further be disposable. In other embodiments, for patients who have implants or implant-supported dentures, the shells may be designed specifically to connect to the implants. Still further, the intraoral appliances may include still other features, such as drug containment and release components.

In some embodiments, the intraoral appliance can comprise upper and lower shells or anchors which are configured to be secured to the patient's upper and lower jaws, respectively. While the shells may be removable, typically being similar to retainers or mouth guards which are temporarily placed over the patient's teeth, either or both of the upper and lower shells can be configured for direct attachment to the patient's bones of the upper and lower jaw. Such attachment is described in co-pending U.S. application Ser. No. 14/992,299, filed Jan. 11, 2016, titled "MANDIBULAR ADVANCEMENT AND RETRACTION VIA BONE ANCHORING DEVICES," the full disclosure of which is incorporated herein by reference. In other instances, the upper and lower shells may be configured to impart the displacement forces through the patient's teeth while minimizing forces which could displace individual teeth relative to the jaw. Such structures are described in co-pending U.S. application Ser. No. 14/992,325, filed Jan. 11, 2016, titled "SYSTEMS, METHODS, AND DEVICES FOR APPLYING DISTRIBUTED FORCES FOR MANDIBULAR ADVANCEMENT," the full disclosure of which is incorporated herein by reference. The upper and lower shells may be removably mounted or permanently implanted, and may have any of the configurations described herein.

Alternatively or in combination, an intraoral appliance can include an upper appliance shell shaped to receive teeth of the patient's upper jaw and a lower appliance shell shaped to receive teeth of the patient's lower jaw. In some embodiments, the appliance includes an advancement apparatus coupling the upper shell and lower shell. The advancement apparatus can be configured to displace the lower shell anteriorly relative to the upper shell, thus advancing the patient's mandible. Optionally, the advancement apparatus can be adapted to constrain the movements of the upper and lower jaws with respect to up to six degrees of freedom, so as to prevent the jaws from returning to the habitual position. The design of the advancement apparatus described herein can be varied as desired to produce the forces for mandibular advancement. For example, an advancement apparatus can include protruding members, recesses, tension members (e.g., elastics, tension springs), compression members (e.g., compression springs) or combinations thereof. An advancement apparatus can include components located on the upper shell and/or lower shell. The components of an advancement apparatus can be located on any portion of the appliance, such as on a buccal surface, lingual surface, occlusal surface, or combinations thereof.

In some embodiments, an advancement apparatus can be used to displace the lower jaw to a plurality of different positions, e.g., along the anterior-posterior direction. Activation of the intraoral appliance may comprise moving the lower shell to and between a plurality of predefined positions. Alternatively, the lower shell may be configured to move continuously from a position of maximum mandibular advancement or protrusion to a position of minimum or neutral protrusion. In various embodiments, the advancement apparatus can be used to displace the lower jaw along an anterior-posterior direction, a vertical direction, and/or a lateral direction. In some embodiments the advancement apparatus can be used to displace the lower jaw along a substantially anterior-posterior direction. The plurality of positions can comprise discrete positions, continuous positions, or a combination thereof. For example, in some embodiments the plurality of positions is a finite set of discrete positions that the lower jaw can assume. In other embodiments, the plurality of positions is a continuous range of positions bounded by one or more upper boundaries and one or more lower boundaries, such as an upper and a lower boundary in the anterior-posterior, vertical and/or lateral directions.

The plurality of different lower jaw positions available provides the advancement apparatus with a range of control over the position of the lower jaw of the patient relative to the upper jaw of the patient. For example, the amount of mandibular advancement, the amount of vertical displacement between upper and lower jaws, and/or the amount of opening of the patient's mouth can all be controlled according to a treatment plan and/or a determined effectiveness of one or more lower jaw positions with respect to treatment of sleep apnea. The optimal position of the lower jaw relative to the lower jaw for treating sleep apnea can vary based on or in response to numerous factors, including patient-specific factors such as the patient's anatomy, the patient's jaw opening trajectory, the degree of advancement tolerated by the patient, the severity and/or frequency of sleep apnea symptoms, and other factors. Machine learning algorithms described further herein can provide optimization of a patient's lower jaw position based on or in response to any of these factors and other factors, and/or combinations thereof.

Moreover, controllable advancement of the mandible to a plurality of different positions allows for the mandibular advancement treatment to be selectively applied and adjusted in response to the patient's real-time sleep apnea status. For example, the mandible can be selectively advanced when the patient is experiencing a sleep apnea event, and can be retracted when the event has terminated. In some embodiments, the lower jaw is advanced for the minimal amount of time and by the minimal amount necessary to effectively treat the sleep apnea event. This approach may reduce or eliminate undesirable side effects of mandibular advancement therapy, such as unintentional tooth repositioning, muscle strain, jaw discomfort, TMJ discomfort, tooth pain, or bite alterations. Machine learning algorithms can be used to provide optimization of the timing and extent of selective mandibular advancement, as described further herein.

An advancement apparatus of a mandibular advancement appliance can be controllably actuated to a plurality of different configurations in order to produce different amounts of jaw displacement (e.g., anterior-posterior and/or vertical displacement). For example, an advancement apparatus can include one or more advancement structures that can be actuated to displace the lower jaw to one or more different positions. Examples of advancement structures include but are not limited to protrusions, posts, levers, rotors, tethers, spindles, screws, gears, wheels, or combinations thereof. Actuation of the advancement structure can involve translating, sliding, rotating, expanding, shrinking, winding, unwinding, bending, folding, unfolding, opening, closing, telescoping, or combinations thereof.

The advancement apparatus can further include at least one actuator to actuate the advancement structures to displace the lower jaw to one or more different positions. The actuator can be a motor, for example, or any other mechanical system that can effect displacement of the mandible. In some embodiments, the motor can be configured to receive control signals from a processor and actuate the advancement structures to a position specified by the control signal. Optionally, the motor can transmit signals to the processor indicative of the current configuration of the advancement structures, e.g., as feedback.

For example, the oral appliances herein can further comprise a motor or other actuator which is coupled between the upper and lower shells and which is configured to respond to the signal delivered by the processor to advance or retract the mandible. The motors can be capable of continuously or incrementally moving the lower shell relative to the upper shell over a range of distances typically from 0.01 mm to 20 mm, usually from 0.05 mm to 8 mm. Specific examples of motors, actuators, and other types of mechanical systems for displacing the mandible are discussed below.

The motor may comprise any self-contained motor or effector which can be coupled to the first and second shells and be energized or otherwise activated to advance the lower shell relative to the upper shell in response to the delivered signal. In some embodiments, the motor may comprise a rotor on either of the upper or lower shells and a follower on the other of the two shells. The rotor can include a lever or other rotating element which can engage a fixed follower in order to effect relative movement. In other embodiments, the motor may comprise a translator on one of the upper and lower shells and a follower on the other of the shells. The translator can be an element which generally translates in anterior and posterior directions in a plane which is coplanar to that of the patient's jaws. As a further alternative, the motor may comprise a spindle on one of the upper and lower shells and a tether which has one end mounted to be reeled in and out by the spinal and another end attached to the other of the shells.

Figure 2A:
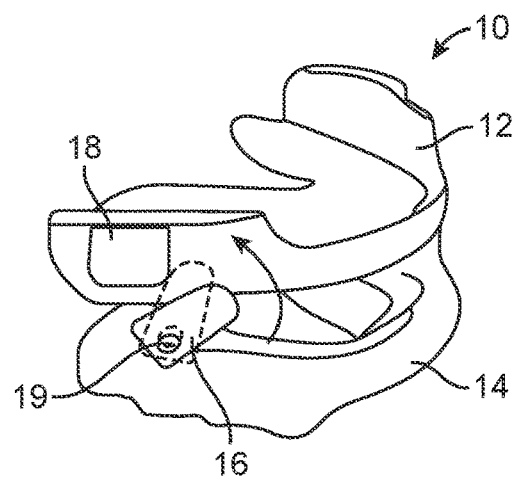
FIGS. 2A, 2B, and 2C illustrate a first exemplary oral appliance having a rotary motor and driver element for changing the relative positions of the upper and lower tooth anchors, in accordance with embodiments.
Figure 2B:
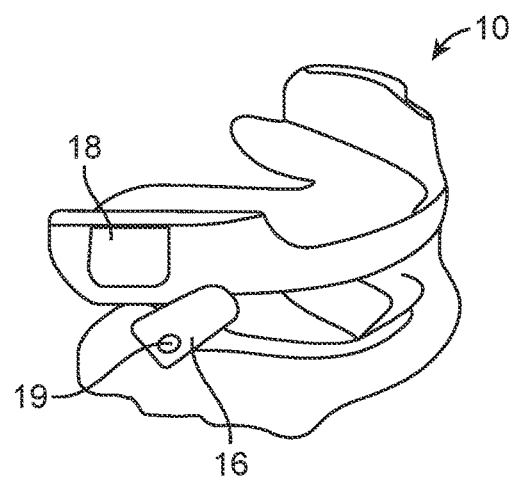
Figure 2C:
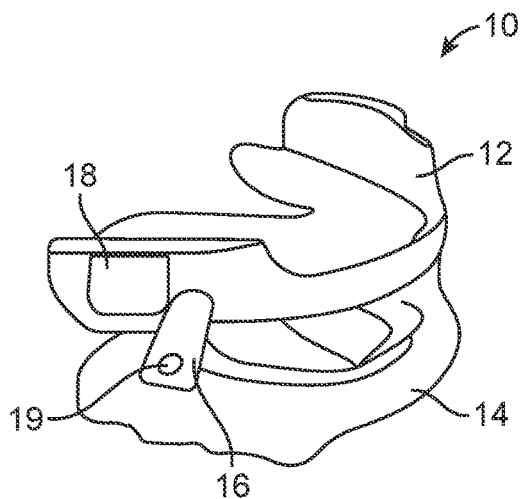

Referring now to FIGS. 2A-2C, a first exemplary intraoral appliance 10 comprises an upper shell 12 and a lower shell 14. As illustrated, the upper and lower shells are retainer-like or aligner-like devices shaped to fit on upper and lower jaws of the patient, respectively. An advancement apparatus coupling the upper and lower shell comprises, in this embodiment, a lower advancement structure coupled to the lower shell 14, the lower advancement structure comprising a rotor element 16 coupled to a pivot 19. Pivot 19 can comprise and/or be coupled to an actuator (not shown) which can rotate rotor element 16 about the pivot axis. As shown in FIG. 2A, rotor element 16 can be rotated in a clockwise direction so that there is significant clearance with upper advancement structure 18 that is coupled to upper shell 12. Thus, in the position shown in FIG. 2A the patient's upper and lower jaws are free to move and the lower shell 14 is not advanced or protruded. This position is also shown in FIG. 2B. By rotating the rotor element 16 in the counter clockwise direction, as shown in FIG. 2C, rotor element 16 of the lower advancement structure can engage upper advancement structure 18 so that the lower shell 14 is displaced relative to upper shell 12, thus displacing the lower jaw of the patient from a first position to a second position anterior to the first position when the appliance is worn. The actuator that rotates rotor element 16 can be configured so that it responds to a first control signal received from one or more processors that can operate as described further herein. The advancement can be reversed by clockwise rotation of rotor element 16 in response to a second control signal received from the one or more processors. Although the rotor element 16 is positioned on the lower shell 14 in the embodiment of FIGS. 2A-2C, it shall be understood that in other embodiments, the rotor element 18 can also be positioned on the upper shell 12. Optionally, both the upper and lower shells can include a respective rotor element that can be rotated to engage each other to produce mandibular advancement.

Figure 3A:
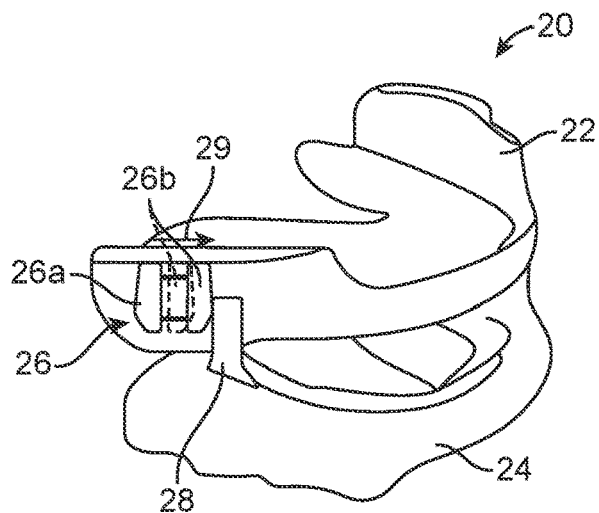
FIGS. 3A, 3B, and 3C illustrate a second exemplary oral appliance having an axially translatable positioning element on an upper anchor constructed, in accordance with embodiments.
Figure 3B:
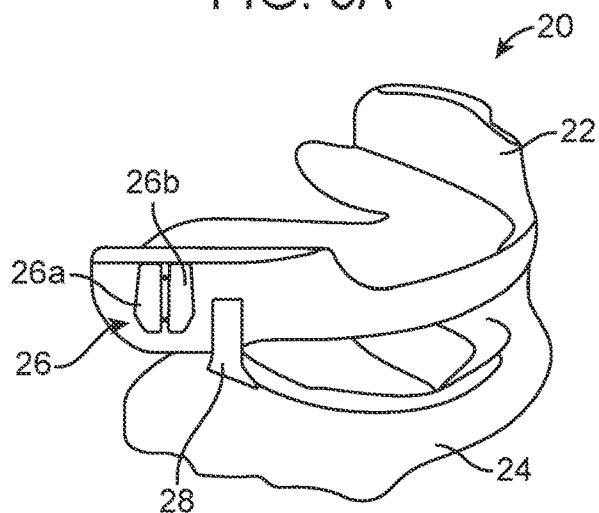
Figure 3C:
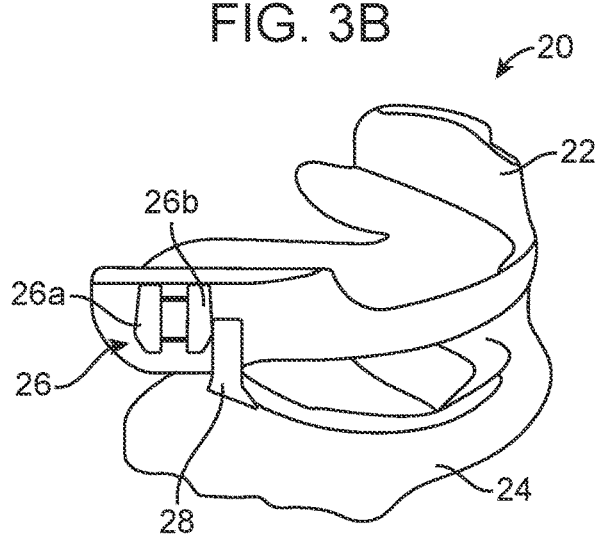

A second exemplary intraoral appliance 20 is illustrated in FIGS. 3A-3C. Intraoral appliance 20 includes an upper shell 22, a lower shell 24, and an advancement apparatus coupling upper shell 22 and lower shell 24, the advancement apparatus comprising, in this embodiment, an upper advancement structure 26 coupled to the upper shell 22 and a lower advancement structure 28 coupled to the lower shell 24. In this embodiment, upper advancement structure 26 includes a fixed component 26a and a moveable component 26b which can be advanced from a retracted position (as shown in broken line in FIG. 3A and in full line in FIG. 3B) to an advanced position (shown in full line in FIG. 3A and in full line in FIG. 3C) by an actuator (not shown) in response to a first control signal received from one or more processors (not shown). In this example, upper advancement structure 26 can comprise and/or be coupled to the actuator. When moveable component 26b is in a sufficiently advanced position, lower advancement structure 28 is engaged by upper advancement structure 26, thereby displacing lower shell 24 relative to upper shell 22 and, in use, displacing the lower jaw of the patient from a first position to a second position anterior to the first position. The displacement can be reversed by retraction of moveable component 26b in response to a second control signal received from the one or more processors. Although the movable component 26b is positioned on the lower shell 24 in the embodiment of FIGS. 3A-3C, it shall be understood that in other embodiments, the movable component 26b can also be positioned on the upper shell 22. Optionally, both the upper and lower shells can include movable components that interact to produce mandibular advancement.

Figure 4A:
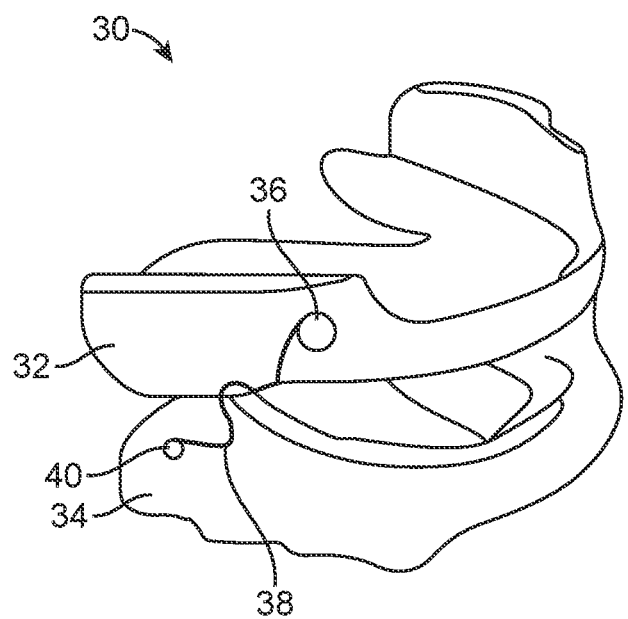
FIGS. 4A and 4B illustrate a third exemplary oral appliance having a spindle and tether mechanism for relative positioning of an upper anchor and lower anchor, in accordance with embodiments.
Figure 4B:
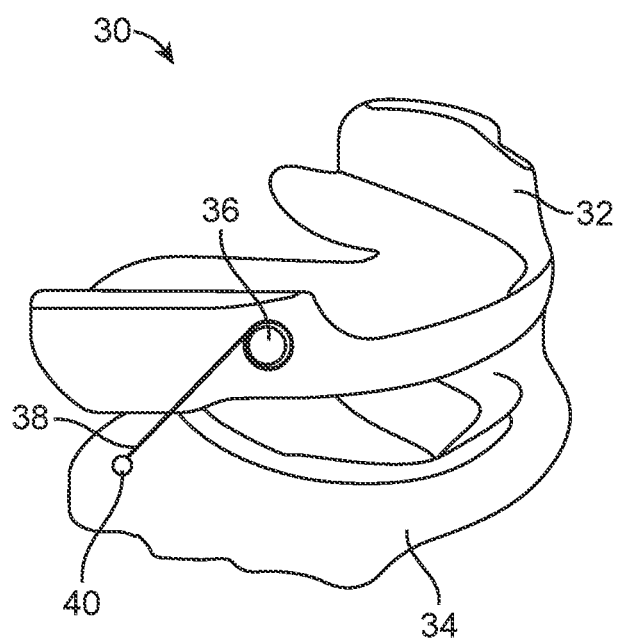

A third exemplary intraoral appliance 30 is illustrated in FIGS. 4A-4B. Intraoral appliance 30 includes an upper shell 32, a lower shell 34, and an advancement apparatus coupling upper shell 32 and lower shell 34, the advancement apparatus comprising, in this embodiment, an actuator 36, a fixed attachment point 40 and a tether element 38. Actuator 36 is located on upper shell 32 and is connected by tether element 38 to fixed attachment point 40 located on lower shell 34. Actuator 36 can adjust the length of tether element 38 in response to control signals received from one or more processors, e.g., by winding and unwinding the tether element 38. For example, actuator 36 can respond to a control signal received from one or more processors by increasing the length of tether element 38 so that upper shell 32 and lower shell 34 are left in an unconstrained state, shown in FIG. 4A. Actuator 36 can also respond to another control signal received from one or more processors by decreasing the length of tether element 38 to displace lower shell 34 relative to upper shell 32, as shown in FIG. 4B. Displacement of lower shell 34 relative to upper shell 32, as shown in FIG. 4B, results in a displacing of the lower jaw from a first position to a second position anterior to the first position. Although the actuator 36 is positioned on the lower shell 34 in the embodiment of FIGS. 2A-2C, it shall be understood that in other embodiments, the actuator 36 can also be positioned on the upper shell 32. Optionally, both the upper and lower shells can include a respective actuator that wind and unwinds the tether element 38 in order to provide controllable displacement of the lower shell 34.

In alternative embodiments, the systems and methods described herein can utilize other types of intraoral appliances besides actuator-based or motorized appliances. A person of ordinary skill in the art would appreciate that the various embodiments of the present disclosure are equally applicable to other types of appliances for treating sleep apnea, such as non-motorized appliances.

Sleep Apnea Monitoring and Treatment System

The present disclosure further provides systems and methods for collecting and analyzing health data and for making healthcare decisions, e.g., relating to the patient's sleep apnea and/or sleep patterns in order to provide controllable and selective mandibular advancement. In some embodiments, the controllable mandibular advancement appliances described herein are implementable as part of a system for monitoring and treating sleep apnea in a patient. In some embodiments, the system is configured to monitor the patient's physiological characteristics and/or sleep status, in order to determine whether a sleep apnea event is imminent. If the onset of a sleep apnea event is detected, the system can control the mandibular advancement appliance to advance the patient's mandible, e.g., by a predetermined amount, or until mitigation of the sleep apnea symptoms is detected. The amount of mandibular advancement can be adjusted as desired for optimal treatment of the sleep apnea. The mandible can then be maintained in an advanced position, e.g., for a predetermined length of time, or until termination of the sleep apnea event is detected, at which point the appliance can be controlled to return the mandible to its habitual position.

In various embodiments, the mandible can be displaced over a range of distances, e.g., from 0.01 mm to 0.1 mm, from 0.1 mm to 0.5 mm, from 0.5 mm to 1 mm, from 1 mm to 5 mm, from 5 mm to 10 mm, and/or from 10 mm to 20 mm anteriorly relative to the habitual position. In some embodiments, the mandible is displaced over a range of distances from 0.05 mm to 5 mm or from 0.05 mm to 8 mm anteriorly relative to the habitual position.

In some embodiments, sensors embedded in the appliance and/or external to the appliance can be configured to, when worn, continuously collect data to build a patient-specific profile including patient status during sleep, e.g. sleep sounds, airflow, temperature, heart rate, EKG, sleep position, and the like. The degree of mandibular advancement can be tracked by sensors in the appliance and/or advancement apparatus or other mechanism or by a processor which generates the advancement signals. The load on the upper and/or lower jaws and arches and in some cases individual teeth can also be tracked by load sensors built into the upper and/or lower shells.

When worn, such collected data may be used for a variety of purposes. In particular, the data may be used to allow "feedback" control of the mandibular advancement motor or other mechanism. Control algorithms may be applied by the processor to optimize patient treatment, such as machine learning algorithms as described herein. For example, the data may be analyzed individually or collectively to determine the timing and/or degree of mandibular advancement needed for the patient at a particular time. In some embodiments, the control may be to activate the device when needed and deactivate the device when the apnea event has terminated. In other embodiments, the control may be to activate the device to an initial required level and then to adjust the device to ease arch/tooth pressure while maintaining sufficient mandibular advancement to suppress the apnea. Additionally or alternatively, the data (and particularly the arch and tooth load data) may be used to minimize load on the arches/teeth while still providing sufficient mandibular advancement to treat the apnea or snoring.

The collected data may also be used to generate patient alarms and reports on patient treatment and status. For example, the collected data may be used to identify irregularities in the sleep patterns and if appropriate take action, e.g., send an alert for help. The data collected over time can be useful to identify problems early on, e.g., worsening breathing patterns, worsening sleeping problems, etc. The data can then be considered by the treating healthcare professional and/or automatically assessed by the processor.

In some embodiments, the appliance may be activatable prior to snoring when the system identifies patient data or parameters that indicate that snoring or other apnea event is about to begin. By collecting data from an individual patient over time, the system can "learn" patient specific patterns of sleep and patient specific patterns of apnea and snoring, e.g., via machine learning algorithms, which can enable the system to predict when an event is likely to occur and enable the system to calibrate and select to what level to activate the device. Similar learning can be used to decide by the system when to deactivate the device.

Other features of the systems of the present disclosure can enable detection of pressure on each side of the appliance, allowing the system to balance the pressure and/or control the pressure. If the pressure on the appliance is high and the patient is in discomfort, the system can cause the oral appliance to reduce the protrusion position, at least for a short period of time to relieve the discomfort. The system may further control the oral appliance to make minor movements, e.g., to eliminate or reduce pressure on one point in the temporomandibular joint (TMJ).

The collection of the data can be used to build a patient-specific profile that can be used for diagnostics, preparation of patient prescriptions, as well as to control and improve performance of the intraoral appliance. For example, the system can adjust and minimize load on the arches while reducing or eliminating sleep problems. The system, when in use, can identify irregularities in the sleep patterns and respond, either by adjusting the oral appliance or by sending an alarm or alert to others. Patient specific data may be collected to allow early identification of problems, such as the worsening of breathing patterns, an increased frequency of breathing, or sleeping problems. Such comparisons can be made relative to prior data from the same patient or statistical data from a population of patients. The construction of a patient-specific profile can be beneficial for providing sleep apnea treatments customized to the patient.

Figure 5:
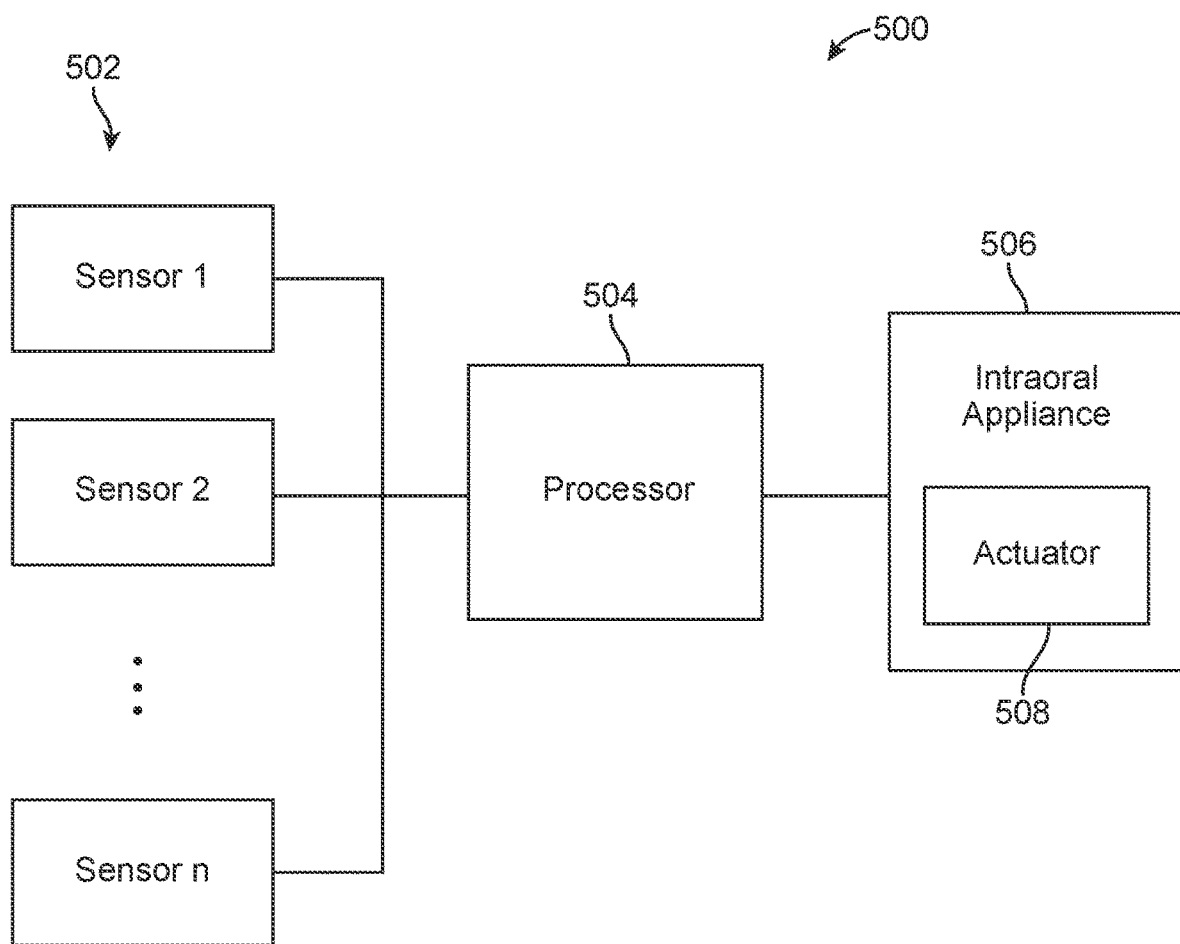
FIG. 5 illustrates a system for monitoring and treating sleep apnea in a patient, in accordance with embodiments.

FIG. 5 illustrates an exemplary system 500, comprising a set of one or more sensors 502 (e.g., n sensors, where n is one, two, three, four, five, or more), a processor 504, and an intraoral appliance 506 comprising an actuator 508. Processor 504 can be referred to herein as a "processor" and/or as a "controller." As used herein, unless otherwise noted, "controller" and "processor" are used interchangeably. In various embodiments, processor 504 can comprise a single processor or a plurality of processors. System 500 can further comprise a memory device (not shown) with executable instructions stored thereon, and the processor 504 can be configured to execute the instructions stored on the memory device. Sensors 502 can be configured to monitor a patient for sleep apnea symptoms, as described further herein. Processor 504 can execute instructions to receive sensor data from sensors 502, and to detect, identify, and/or assess physiological events based on or in response to sensor data, as described further herein. Processor 504 can also execute instructions to transmit control signals to intraoral appliance 506, as described further herein. Processor 504 can perform any one or more of the functions ascribed to it herein by executing one or more algorithms, including but not limited to machine learning algorithms, as described further herein.

Systems of the present disclosure provide one or more processors that can receive sensor data and use the sensor data to detect, predict, and/or assess a patient's symptoms, such as symptoms associated with sleep apnea. For example, in some embodiments, processor 504 can execute instructions to detect physiological events such as onset or termination of a sleep apnea event. In some embodiments, processor 504 can execute instructions to identify physiological discrepancies such as a discrepancy between a current sleeping pattern and a previous sleeping pattern. In some embodiments, processor 504 can execute instructions to make physiological assessments such as an assessment of the likelihood that an apnea event will begin or terminate. Processor 504 can comprise one or more microprocessors and can be configured to receive sensor data related to patient status in the form of one or more signals from sensors 502, either in a wired configuration, a wireless configuration, or a combination thereof. In certain embodiments the processor 504 and one or more of sensors 502 can be part of an integrated system, such as a computer or digital workstation housed in a single housing component.

Systems of the present disclosure provide one or more processors that can transmit a control signal to an intraoral appliance. For example, in some embodiments, processor 504 can execute instructions to detect, predict or assess a pre-apnea or apnea event based on or in response to sensor data received from sensors 502, and can execute instructions to transmit a control signal to intraoral appliance 506 and cause intraoral appliance 506, when in use, to displace the lower jaw of the patient, e.g., to an advanced or protruded position, in order to treat the sleep apnea event and/or suppress snoring. In some embodiments, actuator 508 displaces the lower jaw of the patient in response to the control signal, as further described herein. In various embodiments, when the intraoral appliance 506 is placed in the mouth, processor 504 can control intraoral appliance 506 and/or actuator 508 to, when in place in the patient's mouth, advance the mandible, to retract the mandible, open or close the jaws, and/or adjust a distance or a position in an anterior-posterior direction, a vertical direction, a lateral direction, or a combination thereof, as further described herein. Processor 504 can be configured to deliver a control signal to intraoral appliance 506 and/or actuator 508 via a wired configuration, a wireless configuration, or a combination thereof. Actuator 508 can be, e.g., an embedded mechanism or motor which provides for mandibular displacement, e.g. advancement in an anterior-posterior direction, a vertical direction, a lateral direction, or a combination thereof.

In some embodiments, when the intraoral appliance 506 is positioned in the patient's mouth, processor 504 can send a control signal to intraoral appliance 506 and/or actuator 508 to cause the intraoral appliance to, when in place in the patient's mouth, retract the lower jaw to a habitual or starting jaw position when symptoms of obstructive sleep apnea and/or snoring are observed to be lessening, and/or when termination of a sleep apnea event is detected, based on or in response to sensor data received by processor 504 from sensors 502. For example, processor 504 can send a first control signal to intraoral appliance 506 and/or actuator 508 causing intraoral appliance 506 to advance from a first position to a second position when onset of a sleep apnea event is detected, and processor 504 can send a second control signal to intraoral appliance 506 and/or actuator 508 causing intraoral appliance 506 to retract from the second position to the first position when termination of a sleep apnea event is detected, as described further herein. Alternatively, processor 504 can be configured to send control signals to intraoral appliance 506 and/or actuator 508 causing intraoral appliance 506 to partially or fully retract the mandible after a predetermined time period. The predetermined time period can be within a range from 1 minute to 10 minutes. In some embodiments, the predetermined time period can be approximately 1 minute, 2 minutes, 5 minutes, 10 minutes, 15 minutes, 20 minutes, 30 minutes, 1 hour, or 2 hours.

Systems of the present disclosure provide for collecting data on the patient's apnea patterns over time and using such collected data to improve treatment of sleep apnea and/or snoring. In some embodiments, processor 504 can be configured to collect sensor data from sensors 502 comprising patient data related to the patient's sleep apnea patterns over time. The patient data can be stored on a memory device and/or downloaded or uploaded to the patient's physician, to other treatment management personnel, to system management personnel, and/or to a database such as a cloud database for future retrieval. The patient data can also be used by processor 504, or other processors located elsewhere, using algorithms (including but not limited to machine learning algorithms) and/or other artificial intelligence-based methods to improve treatment protocols for the individual patient. In some embodiments, processor 504 can execute instructions to evaluate patient data and improve methods and/or or algorithms for detection, prediction and/or assessment of physiological events. For example, in some embodiments, processor 504 can evaluate patient data to improve the accuracy of one or more machine learning algorithms in predicting the onset and/or termination of apnea events based on or in response to past symptoms and/or other data related to the particular patient.

Physiological Sensors and Data

Systems, methods, devices and apparatus of the present disclosure can comprise one or more sensors adapted to monitor one or more patient parameters, such as physiological data from the patient. The physiological data can be related to one or more of the patient's sleep patterns, sleep apnea events, normal physiological events, and/or abnormal physiological events. In various embodiments, the sensors monitor physiological data from a patient in real-time, and can transmit this sensor data as one or more signals to be received by one or more processors (e.g., of a suitable sleep apnea monitoring and treatment system). The sensor data can be indicative of events and/or patient symptoms, such as symptoms associated with the onset of a sleep apnea event, and/or a lessening of symptoms associated with a sleep apnea event. In some embodiments, the sensor data is indicative of sleep patterns of the patient and/or physiological information of the patient during sleep.

Sensors utilized in the systems of the present disclosure (e.g., sensor(s) 502 of the system 500) may monitor or track any one of a variety of patient symptoms or status indicators, including sounds, such as snoring, breathing, cessation of breathing, heartbeat, patient position, and the like. In some embodiments, the sensors can monitor breathing patterns, including changes in the pace of breathing, length between breaths, lengths of inhalation, and the like. Other patient symptoms to be sensed can include temperature, temperature changes, and the like. Other data that may not be directly related to sleep apnea can also be measured, including saliva, its content, or other markers. Physiological information that can be monitored by the sensors described herein includes, without limitation: breathing sounds, snoring sounds, breathing rate, respiratory air flow, chest expansion, oxygen level, cardiac data (e.g., heart rate, EKG data), sleeping position, sleeping movements, blood pressure, brain activity (e.g., EEG data) and/or variants thereof and/or combinations thereof.

Any suitable number and combination of sensor types can be used, such as one, two, three, four, five, or more different sensor types. Exemplary sensor types suitable for incorporation with embodiment herein include but are not limited to audio sensors (e.g., microphones), video sensors (e.g., cameras), oxygen sensors (e.g., pulse oximeters), air flow sensors, motion sensors, temperature sensors, strain gauges, force sensors, pressure sensors, heart rate monitors, blood pressure monitors, EKG sensors, EEG sensors, or any other sensor type suitable for obtaining physiological information relating to the patient's sleep status and/or sleep apnea status.

Sensors described herein can be adapted to be positioned outside of a patient's body (externally positioned), inside of a patient's body (internally positioned), or on a patient's body surface. In some embodiments, the sensors may be external to the patient, such as an external microphone to detect breathing sounds, an external camera to detect sleep position, an EKG machine to determine heart rate, and/or variants thereof and/or combinations thereof. In some embodiments, externally positioned sensors are incorporated as part of an external processor, such as a table-mounted processor positioned adjacent to the patient during sleep.

In some embodiments, monitoring is performable by a sensor on or within the patient, such as a sensor mounted on an intraoral appliance worn by the patient. The sensors can be placed on the intraoral appliance and can communicate with external components of the system, such as external processors, wirelessly or via wired. In some embodiments, the sensor is mounted on or positioned in an upper and/or a lower shell of an intraoral appliance. Intraoral monitoring can include monitoring of breathing sounds, respiratory flow rate, sleep position, and/or variants thereof and/or combinations thereof. Internally positioned sensors can be incorporated into the oral appliance in any number of ways and at any number of positions in accordance with embodiments.

The sensors described herein can communicate with and transmit sensor data to a processor via a wired link (such as a USB connection), a wireless link (such as Bluetooth), and/or variants thereof and/or combinations thereof Machine Learning-Based Control of Mandibular Advancement In some embodiments, the systems herein include one or more processors (e.g., the processor 504 of the system 500) that can automatically collect and analyze some or all of the patient parameters which have been sensed by one or more sensors. By tracking these parameters, and identifying changes in these patterns overtime, certain patient parameters and/or symptoms may be correlated with the onset of sleep apnea, snoring, or the like. In those embodiments, these identified patient parameters may be then relied on to help predict the onset of an apnea event in order to begin treatment by mandibular advancement even before other changes are detected. In some embodiments, the processor is configured to implement a machine learning algorithm that identifies patient-specific correlations between physiological parameters and/or symptoms and sleep apnea events, and uses these patient-specific correlations to predict the onset of a sleep apnea event. Symptoms that may be correlated with onset of a sleep apnea event include but are not limited to: changes in blood oxygen level, changes in heart rate, changes in breathing rate or rhythm, changes in body temperature, changes in electrical resistance (e.g., of the skin), increase in sweating, or decrease in sweating. Computer-based approaches such as machine learning algorithms can be used to determine combinations of physiological parameters and/or symptoms that are useful for detecting the onset of sleep apnea events.

Figure 6A:
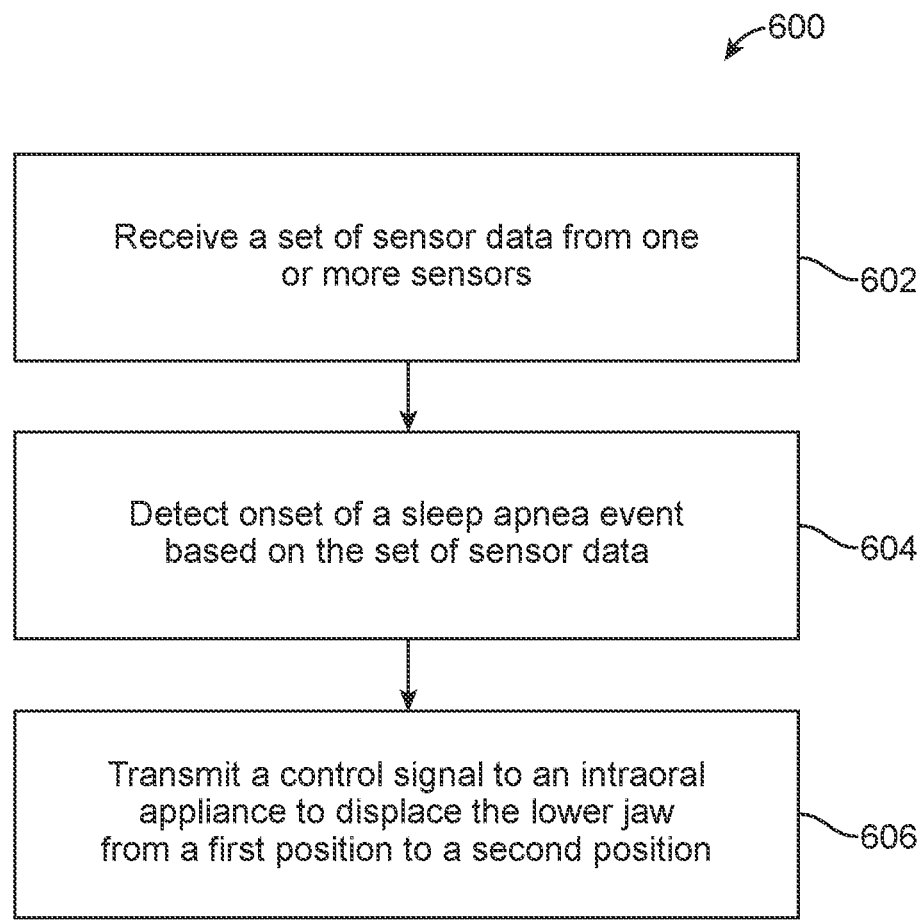
FIGS. 6A, 6B, and 6C illustrate methods for monitoring and treating sleep apnea in a patient, in accordance with embodiments.

FIG. 6A illustrates a method 600 for detecting and treating a sleep apnea event, in accordance with embodiments. The method 600, as with all other methods described herein, can be performed by any embodiment of the systems, devices, and apparatus provided herein. For example, one or more steps of the method 600 can be performed by one or more processors of a system (e.g., processor 504 of the system 500) for monitoring and treating a patient's sleep apnea.

In step 602, a set of sensor data is received from one or more sensors. The sensors can be configured to monitor the patient for symptoms associated with a sleep apnea event, as described herein. Each sensor can provide respective sensor data (e.g., to the controlling processor) throughout the monitoring period at predetermined time intervals, or continuously. The rate at which sensor data is provided can be varied as desired to ensure accurate monitoring of the patient's sleep status and/or sleep apnea status.

In step 604, the onset of a sleep apnea event is detected based on or in response to the set of sensor data. The sensor data can be indicative of physiological parameters and/or symptoms of the patient that are associated with the onset of the sleep apnea event. For instance, the sensor data can indicate that the sleep apnea event has occurred and/or is occurring. Alternatively or in combination, the sensor data can indicate that a sleep apnea event is about to occur and/or is likely to occur. In some embodiments, the step 604 is performed using a computer-implemented algorithm, which may or may not be a machine learning algorithm. A machine learning algorithm can be used, for example, to determine the physiological parameters and/or symptoms represented by the set of sensor data, and/or whether those parameters and/or symptoms are indicative of the onset of a sleep apnea event. For instance, detection of the onset of a sleep apnea event can be performed based on the output of the machine learning algorithm as well as other patient-specific criteria (e.g., patient-specific changes in physiological parameters such as heart rate, breathing rate, etc.). Examples of machine learning algorithms suitable for use with the methods of the present disclosure are described further herein.

In step 606, a control signal is transmitted to an intraoral appliance to cause the intraoral appliance to displace the lower jaw of the patient from a first position to a second position, in order to treat the sleep apnea event. The intraoral appliance can be any embodiment of the mandibular advancement appliances described herein. The first position can be a current position of the patient's jaw. In some embodiments, the first position can be a habitual position of the patient's jaw, e.g., a habitual position assumed during sleep. The second position can be an advanced jaw position in which the mandible is displaced anteriorly relative to the maxilla.

In some embodiments, the second jaw position is a patient-specific position that is customized for the particular patient. Optionally, the second jaw position can be determined using a machine learning algorithm. For example, the machine learning algorithm can be used to determine an amount of mandibular advancement that is optimal for treating the patient's sleep apnea, e.g., in terms of being effective while mitigating side effect such as patient discomfort. The optimal amount of advancement can vary based on or in response to patient-specific factors such as the patient's anatomy, physiology, or level of discomfort tolerated. Additionally, the optimal amount of advancement can vary based on or in response to the specific circumstances of the particular sleep apnea event, such as the severity of the event. Accordingly, the machine learning algorithm can be configured to determine the appropriate advancement amount based on or in response to the physiological parameters and/or symptoms exhibited by the patient, patient-specific factors, the circumstances of the sleep apnea event, or combinations thereof. In some embodiments, the machine learning algorithm can be trained, e.g., using previous data of the patient's sleep apnea events, to determine patient-specific correlations between the amount of mandibular advancement and the treatment effectiveness.

In some embodiments, the step 606 involves causing the intraoral appliance to displace the lower jaw anteriorly until a reduction or cessation of symptoms associated with the sleep apnea event is detected (e.g., via the one or more sensors). For example, the control signal can cause the appliance to incrementally advance the patient's mandible until the sensor data indicates that the sleep apnea symptoms have decreased or ceased, or until a maximum advancement distance has been achieved. The rate of advancement can be sufficiently slow to allow changes in the sleep apnea symptoms to be detected. This approach can be used to reduce or minimize the amount of jaw displacement applied to treat the sleep apnea event, which may be beneficial for mitigating undesirable side effects such as patient discomfort, muscle strain, TMJ dysfunction, tooth repositioning, and/or bite alterations.

The duration for which the jaw is maintained in the advanced position can be varied as desired, and can vary from a few seconds to a few hours depending on the patient. For instance, some patients may only require a few jaw movements to cause the muscles of the upper airway to tighten and prevent the sleep apnea event and/or snoring. In some embodiments, the processors herein are configured to retract the patient's mandible to its original position once the sleep apnea event has subsided and/or after a predetermined time interval. For example, the processor can be configured to maintain the jaw in an advanced position for less than 75%, less than 50%, less than 40%, less than 30%, less than 20%, less than 10%, or less than 5% of the patient's total sleep duration. Alternatively or in combination, the processor can be configured to maintain the jaw in an advanced position for no more than 5 hours, no more than 2 hours, no more than 1 hour, no more than 30 minutes, no more than 20 minutes, no more than 10 minutes, or no more than 5 minutes at a time. In some embodiments, the processor can analyze the received sensor data to determine whether the symptoms of the sleep apnea event are decreasing or have ceased (e.g., with aid of a machine learning algorithm), and retract the patient's jaw accordingly. This approach can reduce the amount of the time the mandible is advanced, which may be beneficial for mitigating undesirable side effects such as patient discomfort, muscle strain, TMJ dysfunction, tooth repositioning, and/or bite alterations.

In alternative embodiments, rather than advancing the jaw to a static advanced position, the method 600 can involve causing the intraoral appliance to displace the mandible through a predefined sequence of movements. The types of movements that are effective for treating the sleep apnea event can vary from patient to patient. Accordingly, the machine learning algorithms described herein can be used to determine patient-specific movement sequences for treating sleep apnea.

Figure 6B:
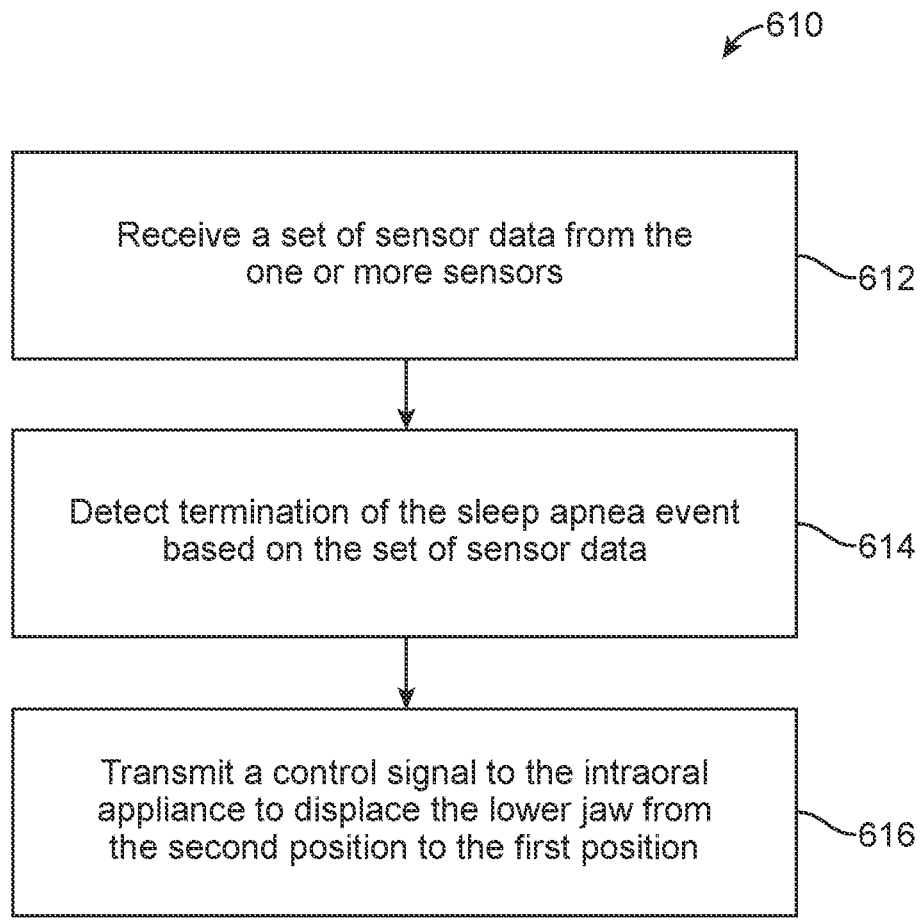

FIG. 6B illustrates a method 610 for terminating treatment of a sleep apnea event, in accordance with embodiments. One or more steps of the method 610 can be performed by one or more processors of a system for monitoring and treating a patient's sleep apnea (e.g., processor 504 of the system 500). In some embodiments, the method 610 is performed after the method 600 to allow for automatic advancement and retraction of the mandible based on or in response to the patient's sleep apnea status.

In step 612, a set of sensor data is received from one or more sensors. Similar to the step 602 of the method 600, each sensor can provide respective sensor data at predetermined time intervals or continuously. The rate at which sensor data is provided can be varied as desired to ensure accurate monitoring of the patient's sleep status and/or sleep apnea status.

In step 614, termination of sleep apnea event is detected based on or in response to the set of sensor data. The sensor data can be indicative of physiological parameters and/or symptoms of the patient that are associated with the termination of the sleep apnea event. For instance, the sensor data can indicate that the sleep apnea event has terminated and/or is terminating, e.g., based on or in response to a lessening of the symptoms associated with the sleep apnea event. Alternatively or in combination, the sensor data can indicate that a sleep apnea event is about to terminate and/or is likely to terminate. In some embodiments, the step 614 is performed using a computer-implemented algorithm, which may or may not be a machine learning algorithm. A machine learning algorithm can be used, for example, to determine the physiological parameters and/or symptoms represented by the set of sensor data, and/or whether those parameters and/or symptoms are indicative of the termination of a sleep apnea event. For instance, detection of the termination of a sleep apnea event can be performed based on the output of the machine learning algorithm as well as other patient-specific criteria. The machine learning algorithm may be the same algorithm used in the method 600, or may be a different algorithm.

In step 616, a control signal is transmitted to an intraoral appliance to cause the intraoral appliance to displace the lower jaw of the patient from the second position to the first position. The first position can be a current or habitual position of the patient's jaw, and the second position can be a mandible-advanced jaw position. In some embodiments, the patient's jaw was previously advanced to the second position in order to treat the sleep apnea event (e.g., according to the method 600), and the step 616 retracts the mandible to the initial position to terminate the mandibular advancement treatment.

In addition to real-time detection of the onset and/or termination of sleep apnea events, the processors herein can be configured to receive and respond to feedback regarding the effectiveness of the mandibular advancement treatment. For example, after the mandible has been advanced, the processor can receive feedback data (e.g., from the one or more sensors) and analyze the feedback data to determine whether the patient's physiological parameters and/or symptoms have improved. If the current treatment is deemed to be not effective (e.g., improvements in the parameters and/or symptoms are not sufficient), the processor can determine further adjustments to the mandible position to try to increase the effectiveness. This process can occur in real time in order allowing for dynamic adjustments to improve treatment of the sleep apnea.

Figure 6C:
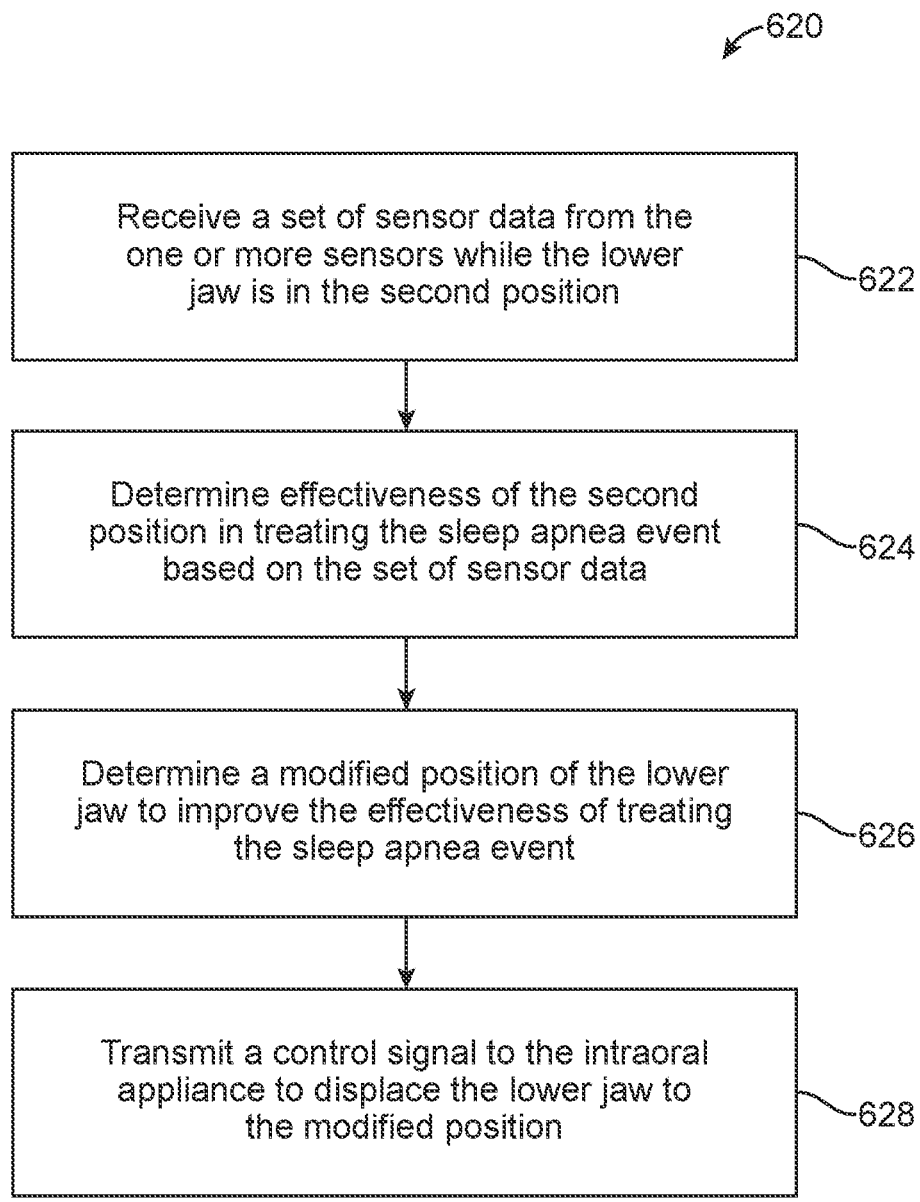

FIG. 6C illustrates a method 620 for improving effectiveness of a sleep apnea treatment, in accordance with embodiments. One or more steps of the method 620 can be performed by one or more processors of a system for monitoring and treating a patient's sleep apnea (e.g., processor 504 of the system 500). In some embodiments, the method 620 is performed after the method 600 and/or prior to the method 610 in order to allow for dynamic modifications to the treatment regimen.

In step 622, a set of sensor data is received from one or more sensors while the lower jaw is in the second position (e.g., the advanced position). The sensors can provide data at predetermined time intervals or continuously, and the rate at which sensor data is provided can be varied as desired to ensure accurate monitoring of the patient's sleep status and/or sleep apnea status.

In step 624, the effectiveness of the second position in treating the sleep apnea event is determined based on or in response to the set of sensor data. The sensor data can be indicative of physiological parameters and/or symptoms of the patient associated with the sleep apnea event. The effectiveness of the treatment can be determined, for example, by detecting whether the patient's physiological parameters are in an improved or normal state, whether the patient's symptoms have lessened in severity, or combinations thereof. An effective treatment may be associated with normal physiological parameters and/or the absence of or a reduction in sleep apnea symptoms, while an ineffective treatment may be associated with abnormal physiological parameters and/or the presence of sleep apnea symptoms. In some embodiments, the step 624 is performed using a computer-implemented algorithm, which may or may not be a machine learning algorithm. A machine learning algorithm can be used, for example, to determine the physiological parameters and/or symptoms represented by the set of sensor data, and/or whether those parameters and/or symptoms are indicative of an effective or ineffective treatment. The machine learning algorithm may be the same algorithm used in the other methods described herein, or may be a different algorithm.

Optionally, the determined effectiveness can be used to update the machine learning algorithm. For example, the determined effectiveness, the jaw position associated with the determined effectiveness, and/or sensor data indicative of the patient's current physiological parameters and/or symptoms can be provided as input data to the machine learning algorithm to improve the performance of the algorithm. The use of feedback data to train and update the machine learning algorithm can further improve the patient-specific characteristics of the algorithm and accuracy of the algorithm in determining effective treatment plans for the patient's sleep apnea.

In step 626, a modified position of the lower jaw to improve the effectiveness of treating the sleep apnea event is determined. For example, the machine learning algorithm or other computer-implemented algorithm can be used to determine a modified position for the mandible that would improve the treatment effectiveness. A machine learning algorithm can be configured to determine a change in the amount of mandibular advancement, such as an increase or a decrease in the amount of mandibular advancement. Optionally, the algorithm can determine a change in other aspects of the jaw configuration, such as an amount of mouth opening, that is predicted to improve effectiveness. The change can be determined based on or in response to the physiological parameters and/or symptoms exhibited by the patient, patient-specific factors, the circumstances of the sleep apnea event, or combinations thereof. In some embodiments, the machine learning algorithm can be trained, e.g., using previous data of the patient's sleep apnea events, to determine patient-specific correlations between the jaw position and the treatment effectiveness In step 628, a control signal is transmitted to the intraoral appliance to displace the lower jaw to the modified position. Subsequently, the method 620 can be repeated as desired to provide continuous feedback of treatment effectiveness and allow the system to adjust the appliance as needed to improve the treatment.

The various types of data collected throughout course of the mandibular advancement treatment can be stored (e.g., on one or memory devices associated with the treatment system) for additional processing and analysis. Such data can include data of the patient's previous sleep patterns (e.g., duration of sleep, physiological parameters during sleep), previous sleep apnea patterns (e.g., number, duration, and/or severity of sleep apnea events, symptoms of sleep apnea events, physiological parameters during sleep apnea events), or previous mandibular advancement treatments applied (e.g., amount and/or duration of advancement, number of advancement cycles, effectiveness of advancement in treating sleep apnea). Optionally, the collected data can include patient preference, such as data of the patient's preferences regarding level of discomfort, perceived effectiveness of the treatment, satisfaction with the treatment, and so on. For instance, the processor can be configured to correlate the length and/or time of mandibular advancement with success in treating the apnea and/or snoring. Thus, as data are collected over time, certain treatment parameters for the specific patient may be optimized and used going forward. Such collection and analysis of the data may be accomplished within the system, such as by the system processor (e.g., a microprocessor), or may be collected and analyzed externally by communication via the internet or other suitable remote access systems. The system may also provide periodic and/or automatic contact with a treating physician in order to provide data, alerts of serious conditions, or the like.

In some embodiments, the collected data (e.g., previous sleep patterns, previous sleep apnea event patterns, previous mandibular advancement treatments applied, patient preferences) is used to update the machine learning algorithm. Updating the machine learning algorithm can comprise training the algorithm using the stored data as training data. Updating the machine learning algorithm can comprise updating the correlations, models, classifications, or other data structures used by the machine learning algorithm to generate the determinations and predictions described herein. This approach allows the system to continue learning and adapting to the patient's sleep patterns and sleep apnea patterns, as well as to continue improve the effectiveness of the mandibular advancement treatment regimen in treating the sleep apnea. Accordingly, the treatment system can become increasingly customized to the patient as the system is used over time.

Optionally, collected patient-specific data can be added to a database of sleep apnea-related data for multiple patients, and this database can be processed and analyzed to determine information that may be useful for improving the understanding of sleep apnea and design of effective treatments. The analysis results can be used to develop patient-specific treatments, such as treatments based on the selective mandibular advancement systems, methods, and devices described herein.

Other features which may optionally be provided by the system include waking up the patient in certain circumstances, such as when the patient assumes a supine position, activation of other devices or functions which may contribute to cessation of snoring and apnea, providing alerts either locally or remotely, under certain circumstances. In some embodiments, the processor can be configured to execute instructions to identify physiological discrepancies in the patient, e.g., based on or in response to received sensor data. Such discrepancies can include a discrepancy between the normal or expected physiological parameters of the patient and the current physiological parameters of the patient. In some embodiments, the discrepancy can be between a normal or expected sleeping pattern of the patient and a current sleeping pattern of the patient. In various embodiments, the processor uses a machine learning algorithm to identify such discrepancies, e.g., by comparing historical and/or predicted data with the patient's current state. If a discrepancy is detected, the processor can generate an alert indicative of the discrepancy, e.g., on a user device such as a digital processing device. The alert can be transmitted to the patient and/or the patient's care provider to inform them of any potential medical issues for follow up. Optionally, if the discrepancy is indicative of a medical emergency, immediate action can be taken. For example, the alert can be used to wake the patient, contact the patient's care provider, and/or contact emergency personnel.

Many different types of machine learning algorithms can be implemented by the systems described herein to perform the patient-customized monitoring and treatment of the present disclosure. Machine learning algorithms described herein can comprise supervised learning methods, including but not limited to classification and regression. Machine learning algorithms described herein can comprise unsupervised learning methods, including but not limited to clustering. Exemplary machine learning methods provided herein are non-limiting, and other methods and approaches known to those of skill in the art can be used to generate and apply predictive models and to make physiological assessments and are within the scope of the systems, methods, devices and apparatus described herein.

Machine learning algorithms described herein can comprise reinforcement learning algorithms, representation learning algorithms, similarity learning algorithms, metric learning algorithms, recommendation systems, sparse dictionary learning algorithms, genetic algorithms, inductive logic programming, and/or variants thereof and/or combinations thereof.

Machine learning algorithms described herein can comprise supervised learning methods, including, without limitation, classification methods, regression, regression methods, and/or variants thereof and/or combinations thereof.

Machine learning algorithms described herein can comprise decision tree learning that can be used to map observations about physiological data from a patient in order to make predictions. Decision tree learning can comprise but is not limited to classification tree learning and regression tree learning.

Machine learning algorithms described herein can comprise association rule learning that can be used to identify relationships between variables obtained from physiological data in order to make predictions. Association rule learning can comprise, but is not limited to, a priori algorithms, equivalence class transformation algorithms, frequent pattern growth algorithms, a priori dynamic programming, context based association rule mining algorithms, node-set based algorithms, general unary hypotheses automata including ASSOC procedures, OPUS, and/or variants thereof and/or combinations thereof.

Machine learning algorithms described herein can comprise classification methods, including but not limited to nearest neighbors classifications, or k-nearest neighbors classifications. In some aspects, nearest neighbor classifications are used for classification and/or regression of physiological data that can be used to make predictions.

Machine learning algorithms described herein can comprise linear regressions that can model a relationship between one or more dependent variables with one or more independent variables. The linear regressions can be simple linear regressions that have one independent variable, or multiple linear regressions that have a plurality of independent variables. The linear regressions can be multivariate linear regressions that have a plurality of dependent variables that may be correlated with one another. In some aspects, one or more variables obtained from physiological data are analyzed using linear regression to determine whether the one or more variables are linearly related, and related variables can be used to make physiological predictions.

Machine learning algorithms described herein can comprise naive Bayes classifications that can be used for classification of physiological data. In some aspects, naive Bayes classification can be used to determine the likelihood of an event given a set of physiological data obtained from a patient.

Machine learning algorithms described herein can comprise logistic regression that can be used to predict a physiological state from two possible state classifications based on physiological data. In some aspects, logistic regression is used to determine the likelihood of onset and/or termination of a sleep apnea event based on physiological data.

Machine learning algorithms described herein can comprise perceptron classification that can be used to predict a physiological state from more than two possible state classifications based on physiological data. In some aspects, perceptron classification is used to determine the likelihood of onset and/or termination of a sleep apnea event based on physiological data.

Machine learning algorithms described herein can comprise support vector machines (SVMs). In some instances the SVM provides a linear classification that separates physiological data points having N dimensions into classes based on distance of the data points from a hyperplane having N−1 dimensions. The hyperplane can be chosen so that the distances from the hyperplane to the nearest data points on either side of the hyperplane are maximized, and points lying on opposite sides of the hyperplane are grouped as belonging to distinct classes. In some aspects, points lying on opposite sides of the hyperplane are grouped as belonging to distinct classes corresponding to a "high risk" state versus a "low risk" state for onset of a sleep apnea event. In some aspects the SVM uses a soft margin method for choosing the hyperplane.

In some embodiments, the SVM provides a nonlinear classification that separates the data points with a hyperplane in a transformed feature space. The transformed feature space can be determined by one or more kernel functions, including nonlinear kernel functions. The transformation can be nonlinear and the transformed space high dimensional, such that the classifier can be a hyperplane in the high-dimensional feature space, but can be nonlinear in the original input space. The kernel functions can comprise, without limitation, homogeneous polynomial functions, inhomogeneous polynomial functions, Gaussian radial basis functions, hyperbolic tangent functions, and/or variants thereof and/or combinations thereof.

In some embodiments, the SVM is a multiclass SVM that separates data points into more than two classes. In some embodiment, the multiclass SVM reduces the multiclass problem into multiple binary classification problems. In some embodiments, the multiclass SVM is a directed acyclic graph SVM or a variant thereof. In some embodiments, the multiclass SVM uses error-corrected output codes.

Machine learning algorithms described herein can comprise relevance vector machines (RVMs). RVMs can be of similar functional form as SVMs described herein, but can provide probabilistic classifications, such as classifications based on Bayesian inference.

Machine learning algorithms described herein can comprise clustering methods, including but not limited to balanced iterative reducing and clustering using hierarchies (BIRCH). BIRCH can be used to incrementally and dynamically cluster incoming, multi-dimensional physiological data from a patient and to cluster the data optimally for given set of constraints, such as processing constraints, memory constraints and/or speed constraints.

Machine learning algorithms described herein can comprise hierarchical clustering, or hierarchical cluster analysis, that can be used to build a hierarchy of clusters of physiological data. In some embodiments, the hierarchical clustering implements an agglomerative or "bottom up" approach wherein each data point starts in its own cluster, and pairs of clusters are merged at progressively higher levels of the hierarchy. In some embodiments, the hierarchical clustering implements a divisive or "top down" approach wherein all data points start in one cluster, and clusters are split at progressively lower levels of the hierarchy.

Machine learning algorithms described herein can comprise k-means clustering that can be used to physiological data into k clusters, where k is an integer equal or greater than two. After k-means clustering each data point belongs to a cluster having a mean that is closer to the data point than any of the other clusters' means are.

Machine learning algorithms described herein can comprise expectation-maximization (EM) clustering that can be used to determine a maximum likelihood estimate of unobserved latent variables (e.g. unknown physiological parameters) based on a marginal likelihood derived from observed physiological data.

Machine learning algorithms described herein can comprise density-based clustering, such as density-based clustering with noise (DBSCAN) and/or ordering points to identify the clustering structure (OPTICS). Density-based clustering can be used to group together physiological data points that are close to one another and identify data points that are far away from other data points as outliers.

Machine learning algorithms described herein can comprise mean-shift analysis that can be used to determine the maxima of a density function based on discrete physiological data sampled from that function. In some aspects mean-shift analysis can be used to determine one or more maxima corresponding to local or global maxima of density in a plurality of data points lying in a coordinate system for purpose of clustering.

Machine learning algorithms described herein can comprise methods of dimensionality reduction, including but not limited to factor analysis, canonical correlation analysis, principal component analysis, independent component analysis, linear discriminant analysis, Fischer's linear discriminant analysis, non-negative matrix factorization/approximation, t-distributed stochastic neighbor embedding, and/or variants thereof and/or combinations thereof.

Machine learning algorithms described herein can comprise structured prediction and/or structured learning techniques that can be used to predict structured objects and/or structured data, such as structured physiological data. Structured objects and structured data may not be simple data types such as discrete scalar values or real scalar values. Structured objects and structured data may be more complex than simple data types such as discrete scalar values or real scalar values. Structured prediction and/or structured learning techniques can comprise, without limitation, sequence labeling, parsing, collective classification, bipartite matching, graphical models, probabilistic graphical models, Bayesian networks, belief networks, Bayesian models, probabilistic directed acyclic graphical models, conditional random fields, hidden Markov models and/or variants thereof, and/or combinations thereof.

Machine learning algorithms described herein can comprise anomaly detection and/or outlier detection that can be used to identify physiological data that do not conform to an expected pattern or are otherwise distinct from other physiological data in a dataset. Anomaly detection and/or outlier detection can comprise, without limitation, density-based techniques, k-nearest neighbors classification, local outlier factor analysis, subspace-based outlier detection, correlation-based outlier detection, support vector machines, replicator neural networks, cluster analysis, deviations from association rules, deviations from frequent item sets, fuzzy logic based outlier detection, ensemble techniques, feature bagging, score normalization, and/or variants thereof and/or combinations thereof.

Machine learning algorithms described herein can comprise neural networks that can be used to estimate or approximate functions that depend on inputs. The neural networks can comprise one or more layers of artificial "neurons" that receive input data and generate output data. The neural networks can comprise feed-forward and/or feed-back connectivity between "neurons" and/or layers thereof. In some embodiments, the inputs comprise a large number of inputs. The inputs and outputs can comprise physiological data and/or functions thereof. In some aspects the functions are unknown. Neural networks can comprise, without limitation, autoencoder networks, autoassociator networks, Diablo networks, deep learning networks, deep structured learning networks hierarchical learning networks, feedforward artificial neural network models, multilayer perceptrons, recurrent neural networks, In some instances, restricted Boltzmann machines, self-organizing maps, or self-organizing feature maps, convolutional neural networks, and/or variants thereof and/or combinations thereof.

Machine learning algorithms described herein can comprise deep learning methods including but not limited to deep belief networks, deep belief networks, convolutional neural networks, convolutional deep belief networks, deep Boltzmann machines, stacked (denoising) auto-encoders, deep stacking networks, tensor deep stacking networks, Gaussian restricted Boltzmann machines, spike-and-slab restricted Boltzmann machines, compound hierarchical-deep models, deep coding networks, deep kernel machines, deep Q-networks, and/or variants thereof and/or combinations thereof.

Machine learning algorithms described herein can comprise ensemble learning methods that incorporate a plurality of the machine learning methods described herein to obtain better predictive performance than can be achieved from any one of the machine learning methods described herein. The ensemble learning methods can comprise, without limitation, Bayes optimal classifiers, bootstrap aggregating ("bagging"), boosting, Bayesian model averaging, Bayesian model combination, cross-validation selection ("bucket of models"), stacking (stacked generalization), and random forests. In some embodiments, the ensemble learning method comprises random forests that operate by constructing a plurality of decision trees and outputting the class that is the mode of the classes (classification) or mean prediction (regression) of the individual trees.

In alternative embodiments, the systems and methods described herein may not use a machine learning algorithm to perform the patient-customized monitoring and treatment of the present disclosure. In some embodiments, the systems and methods described herein may use an algorithm, process and/or method that is not a machine learning algorithm instead of or in addition to a machine learning algorithm to perform the patient-customized monitoring and treatment of the present disclosure.

Digital Processing Devices

In some embodiments, the systems, methods, devices and apparatus described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the systems, methods, devices, and apparatus disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the systems, methods, devices and apparatus disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

In some embodiments, the systems, methods, devices, and apparatus disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the systems, methods, devices, and apparatus disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A non-transitory computer readable medium comprising instructions that when executed by a processor, carry out a method comprising:

receiving a set of sensor data from one or more sensors configured to monitor a patient for symptoms associated with sleep apnea;

detecting, using a machine learning algorithm executed by one or more processors, onset of a sleep apnea event based on the set of sensor data; and transmitting a control signal to an intraoral appliance worn by the patient to cause the intraoral appliance to displace a lower jaw of the patient from a first position to a second position in order to treat the sleep apnea event.

2. The non-transitory computer readable medium of claim 1, wherein the sensor data includes breathing sounds, snoring sounds, breathing rate, respiratory air flow, chest expansion, oxygen level, cardiac data, or sleeping position, or combinations thereof.

3. The non-transitory computer readable medium of claim 1, wherein the machine learning algorithm is customized to the patient using data of previous sleep patterns of the patient.

4. The non-transitory computer readable medium of claim 3, wherein the instructions that when executed by a processor further carry out:

identifying a discrepancy between a current sleeping pattern of the patient and the previous sleep patterns of the patient; and generating an alert indicative of the discrepancy.

5. The non-transitory computer readable medium of claim 1 wherein the first position is a habitual jaw position and the second position is an advanced jaw position.

6. The non-transitory computer readable medium of claim 5, wherein the instructions that when executed by a processor further carry out:

receiving a second set of sensor data from the one or more sensors;

detecting, using the machine learning algorithm, termination of the sleep apnea event based on the second set of sensor data; and transmitting a second control signal to the intraoral appliance to cause the intraoral appliance to displace the lower jaw of the patient from the second position to the first position.

7. The non-transitory computer readable medium of claim 1, wherein the instructions that when executed by a processor further carry out:

determining the second position for the lower jaw using the machine learning algorithm.

8. The non-transitory computer readable medium of claim 7, wherein the instructions that when executed by a processor further carry out:

receiving a third set of sensor data from the one or more sensors while the lower jaw is in the second position; and determining effectiveness of the second position of the lower jaw in treating the sleep apnea event based on the third set of sensor data.

9. The non-transitory computer readable medium of claim 8, wherein the instructions that when executed by a processor further carry out:

updating the machine learning algorithm based on the determined effectiveness.

10. The non-transitory computer readable medium of claim 9, wherein the instructions that when executed by a processor further carry out:

determining, using the machine learning algorithm, a modified position of the lower jaw to improve the effectiveness of treating the sleep apnea event; and transmitting a third control signal to the intraoral appliance to displace the lower jaw to the modified position.

11. A non-transitory computer readable medium comprising instructions that when executed by a processor, carry out a method comprising:
- receiving a first set of sensor data from a one or more sensors,
- detecting, using a machine learning algorithm, onset of a sleep apnea event based on the first set of sensor data, and
- transmitting a first control signal to an intraoral appliance worn by a patient to instruct an actuator on the intraoral appliance to provide a first displacement force to displace a lower jaw of the patient from a first position to a second position in order to treat the sleep apnea condition.

12. The non-transitory computer readable medium of claim 11, wherein the sensor data includes breathing sounds, snoring sounds, breathing rate, respiratory air flow, chest expansion, oxygen level, cardiac data, or sleeping position, or combinations thereof.

13. The non-transitory computer readable medium of claim 11, wherein the machine learning algorithm is customized to the patient using data of previous sleep patterns of the patient.

14. The non-transitory computer readable medium of claim 13, wherein the instructions that when executed by a processor further carry out:
- identifying a discrepancy between a current sleep pattern of the patient and the previous sleep patterns of the patient; and
- generating an alert indicative of the discrepancy.

15. The non-transitory computer readable medium of claim 11, wherein the instructions that when executed by a processor further carry out:
- receiving a second set of sensor data from the one or more sensors;
- detecting, using the machine learning algorithm, termination of the sleep apnea event based on the second set of sensor data; and
- transmitting a second control signal to the intraoral appliance to cause the intraoral appliance to displace the lower jaw of the patient from the second position to the first position.

16. The non-transitory computer readable medium of claim 11, wherein the instructions that when executed by a processor further carry out:
- determining the second position for the lower jaw using the machine learning algorithm.

17. The non-transitory computer readable medium of claim 16, wherein the instructions that when executed by a processor further carry out:
- receiving a third set of sensor data from the one or more sensors while the lower jaw is in the second position; and
- determine effectiveness of the second position of the lower jaw in treating the sleep apnea event based on the third set of sensor data.

18. The non-transitory computer readable medium of claim 17, wherein the instructions that when executed by a processor further carry out:
- updating the machine learning algorithm based on the determined effectiveness.

19. The non-transitory computer readable medium of claim 17, wherein the instructions that when executed by a processor further carry out:
- determining, using the machine learning algorithm, a modified position of the lower jaw to improve the effectiveness of treating the sleep apnea event; and
- transmit a third control signal to the intraoral appliance to displace the lower jaw to the modified position.

20. The non-transitory computer readable medium of claim 11, wherein the first position is a habitual jaw position and the second position is an advanced jaw position, and displacing the lower jaw comprises advancing the lower jaw from the habitual jaw position to the advanced jaw position.

* * * * *